United States Patent
Stoddart et al.

(10) Patent No.: US 10,228,343 B2
(45) Date of Patent: Mar. 12, 2019

(54) ELECTROCHEMICAL DETECTION OF CARBON DIOXIDE USING A CARBOHYDRATE BASED COORDINATION POLYMER

(71) Applicants: NORTHWESTERN UNIVERSITY, Evanston, IL (US); KING ABDULAZIZ CITY FOR SCIENCE AND TECHNOLOGY (KACST), Riyadh (SA)

(72) Inventors: James Fraser Stoddart, Evanston, IL (US); Jeremiah J. Gassensmith, Allen, TX (US); Nak Cheon Jeong, Daegu (KR); Omar K. Farha, Glenview, IL (US)

(73) Assignees: Northwestern University, Evanston, IA (US); King Abdulaziz City for Science and Technology (KACST), Riyadh (SA)

(*) Notice: Subject to any disclaimer, the term of this patent is extended or adjusted under 35 U.S.C. 154(b) by 370 days.

(21) Appl. No.: 14/844,949

(22) Filed: Sep. 3, 2015

(65) Prior Publication Data
US 2016/0061770 A1    Mar. 3, 2016

Related U.S. Application Data

(60) Provisional application No. 62/045,517, filed on Sep. 3, 2014.

(51) Int. Cl.
*G01N 27/407* (2006.01)
*G01N 27/403* (2006.01)

(52) U.S. Cl.
CPC ..... *G01N 27/4074* (2013.01); *G01N 27/4073* (2013.01)

(58) Field of Classification Search
CPC ........... G01N 27/4073; G01N 27/4074; G01N 27/407
See application file for complete search history.

(56) References Cited

U.S. PATENT DOCUMENTS

| | | | |
|---|---|---|---|
| 9,085,460 B2 | 7/2015 | Stoddart et al. | |
| 2010/0155239 A1* | 6/2010 | Sorensen | G01N 27/304 204/403.06 |
| 2012/0070904 A1* | 3/2012 | Stoddart | B01J 20/226 436/133 |
| 2012/0263870 A1* | 10/2012 | Hunter | G01N 27/4074 427/125 |

(Continued)

OTHER PUBLICATIONS

Gassensmith et al., "Strong and Reversible Binding of Carbon Dioxide in a Green Metal-Organic Framework," J. Am. Chem. Soc. 2011, 133:153121-15315.

(Continued)

*Primary Examiner* — Susan D Leong
(74) *Attorney, Agent, or Firm* — Andrus Intellectual Property Law, LLP

(57) ABSTRACT

An electrochemical sensor for an analyte is provided. The electrochemical sensor includes CDMOF-2. The CDMOF-2 is capable of binding reversibly to $CO_2$ as an analyte, thereby quantitatively detecting the analyte in a mixture. The CDMOF-2 is formed from reaction of γ-cyclodextrin with RbOH in the presence of methanol.

9 Claims, 6 Drawing Sheets

(56) References Cited

U.S. PATENT DOCUMENTS

2012/0301543 A1* 11/2012 Metz .................. A61K 9/025
 424/456
2014/0311574 A1* 10/2014 Gordon ................ C09B 23/005
 136/261

OTHER PUBLICATIONS

Gassensmith et al. "A metal-organic framework-based material for electrochemical sensing of carbon dioxide," J. Am. Chem. Soc. 2014 136:8277-8282.
Smaldone et al., "Metal-Organic Frameworks from Edible Natural Products," Angew. Chem., Int. Ed. 2010 49:8630-8634.

* cited by examiner

ELECTROCHEMICAL DETECTION OF CARBON DIOXIDE USING A CARBOHYDRATE BASED COORDINATION POLYMER

CROSS-REFERENCE TO RELATED APPLICATIONS

This application claims benefit of priority under 35 U.S.C. 119 to U.S. provisional patent application Ser. No. 62/045,517, filed Sep. 3, 2014, and entitled "ELECTROCHEMICAL DETECTION OF CARBON DIOXIDE USING A CARBOHYDRATE BASED COORDINATION POLYMER," the contents of which are herein incorporated by reference in its entirety.

STATEMENT REGARDING FEDERALLY SPONSORED RESEARCH OR DEVELOPMENT

This invention was made with government support under contract number DE-FG02-08ER15967 awarded by the Department of Energy. The government has certain rights in the invention.

BACKGROUND

1. Technical Field

The present disclosure relates to methods for preparing metal organic frameworks as sensors for the quantitative detection of analytes, particularly $CO_2$.

2. Description of Related Art

The detection of carbon dioxide within mixtures of gases has proven difficult owing to the presence typically of competing oxygen, carbon monoxide and water vapor. It stands to reason, therefore, that the clear benefits of having robust and inexpensive devices to provide a quantitative analysis of $CO_2$ concentrations in admixture with other gases provides more than enough impetus for the continued development of such devices. Much of the present sensing technology depends largely upon spectroscopic methods that become unreliable when the mixture of gases contains spectroscopically similar resonances. The complication and expense of fabricating the necessary devices for the detection of $CO_2$ in applications where they could be most useful makes these devices highly sought after in their own right. For example, in the medical arena, new sensing technologies could improve human health by enabling the analysis of human breath when a patient is showing clinical signs of hypercapnia. Likewise, in the field of occupational safety, the buildup of $CO_2$ emissions in the form of "blackdamp" in the mining and petroleum industries can be hazardous, particularly as we progress more and more toward coal liquefaction and the extraction of natural gas from shale oil deposits. Here, we describe a method to detect carbon dioxide within $CO_2/N_2$ and $CO_2$/air mixtures using a recently described metal organic framework[5] (MOF) composed of cyclodextrin (CD) and alkali metal (Group1A) cations.

Smaldone et al. (*Angew. Chem., Int. Ed.* 2010, 49:8630-8634) reported of a new cyclodextrin derived material called CDMOF-2 that exhibits strong but reversible binding of carbon dioxide. Though the authors were able to crudely demonstrate a colorimetric response of CDMOF-2 in the presence of $CO_2$ by taking advantage of the unique chemistry that occurs within this highly porous material (Gassensmith et al., *J. Am. Chem. Soc.* 2011, 133:153121-5315), this response is by no means sufficient for practical quantitative analysis. This highly porous material belongs to a rapidly growing family of MOFs that are highly crystalline materials that are well structured chemically with building blocks—typically clusters of metal ions (components of the nodes) and rigid organics ligands (components of the extendable structural frameworks). Important features of MOFs are their (i) highly ordered nanoporosity, (ii) their large internal surface area, and (iii) the possibility of modifying their organic ligands post-synthetically. Accordingly, MOFs have been evaluated as potential nanoporous materials for applications in chemical separations, gas adsorption heterogeneous catalysis, ion exchange, drug delivery, ionic conduction, and sensing. More specifically, MOFs are receiving a lot of attention as a method for $CO_2$ sequestration and colorimetric sensing.

No instances of conductance-based MOFs for $CO_2$ detection have been reported in the literature. The need for an electrochemical means of sensing $CO_2$ comes, in part, from an emerging environmental requirement to monitor concentrations at and near high volume, emission point sources, and from the limitations in present state of the art technologies. Although chemiresistive metal oxides and semiconducting field effect transistors have been thoroughly investigated, they have a limitation to their application—namely, from reaction with ambient oxygenated species absorbed on the oxide surface. In order to circumvent this limitation, semiconducting oxide sensors usually operate at temperatures in excess of 200° C. As an alternative, MOFs have been shown to be an excellent choice for sensing analytes at relatively low temperatures.

The majority of previously-designed MOFs for the selective uptake of $CO_2$ have not exhibited reversible chemisorption desorption of carbon dioxide.

BRIEF SUMMARY

In a first aspect, an electrochemical sensor for an analyte is provided. The electrochemical sensor includes CDMOF-2.

In a second aspect, a method of quantitatively detecting an analyte in a medium is provided. The method includes the step of contacting a CDMOF-2 with the medium.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The features, objects and advantages other than those set forth above will become more readily apparent when consideration is given to the detailed description below. Such detailed description makes reference to the following drawings.

Figure 1:
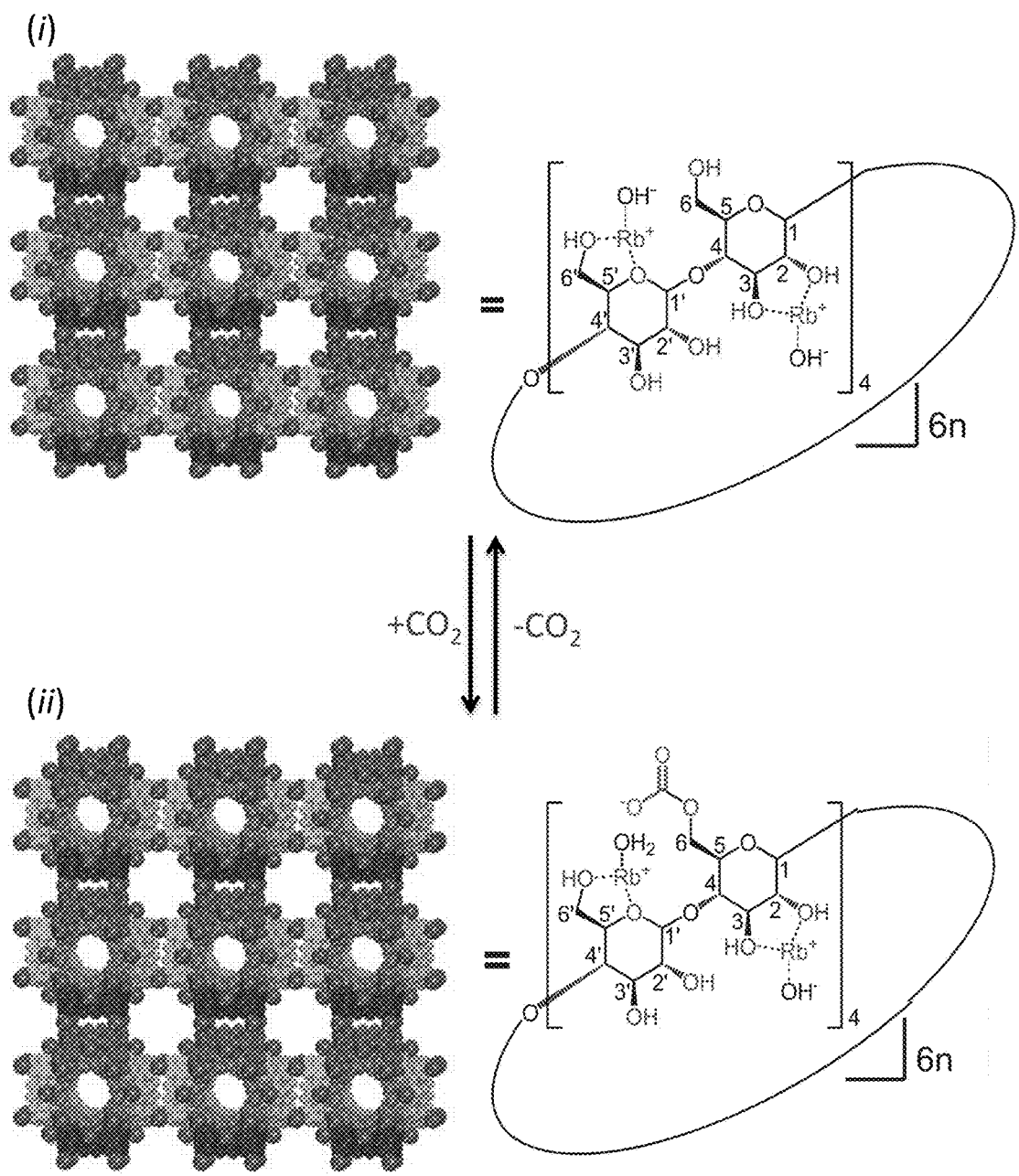
FIG. 1 depicts an exemplary schematic diagram illustrating the equilibrium proposed to exist during the chemisorption of $CO_2$ by CDMOF-2, expressed in the context of the structural formula of one of the four repeating maltosyl units present in a single CD torus. The $[(Rb^+)_4(CD)]_6$ unit in which the six CD rings forming the sides of the cube are portrayed in different colors, wherein $[(Rb^+)_4(CD)]_{6n}$ is shown assembled in a planar fashion. The C and O atoms in the framework are depicted in different colors; the Rb atoms are depicted in larger purple color; the O atoms of the hydroxyl group available for $CO_2$ binding are depicted in red.

While the present invention is amenable to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments and claims herein for interpreting the scope of the invention.

DETAILED DESCRIPTION

The compositions and methods now will be described more fully hereinafter with reference to the accompanying drawings, in which some, but not all permutations and variations of embodiments of the invention are shown. Indeed, the invention may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, "CD-MOF" or "CDMOF" refers to γ-cyclodextrin-based metal-organic framework comprising a plurality of metal cations and a plurality of γ-cyclodextrin molecules. The compound referred to as "CD-MOF-2" or "CDMOF-2" comprises γ-cyclodextrin-based metal-organic framework comprising a plurality of metal cations and a plurality of γ-cyclodextrin molecules, wherein the metal cations are $Rb^+$ cations. The compound referred to as "CA-CDMOF-2" is a carbonic acid derivative of CDMOF-2 formed by covalent binding of $CO_2$ to at least one non-coordinated free primary hydroxyl group present in the γ-cyclodextrin portion of CDMOF-2.

Overview

Applicants developed a new electrochemical sensor and method for detecting $CO_2$ using CDMOF-2, which is a γ-cyclodextrin-Rb metal oxide framework (MOF) complex formed from reacting γ-cyclodextrin and RbOH in the presence of methanol. The free primary alcohol hydroxyl groups present in the CDMOF-2 can reversibly bind to $CO_2$ to form carbonic acid derivatives of CDMOF-2. The "as synthesized" CDMOF-2 that exhibits high proton conductivity in pore filling methanolic media displays a dramatic decrease in its ionic conductivity on binding $CO_2$. This fundamental property has been exploited to create ratiometric sensor capable of measuring $CO_2$ concentrations quantitatively even in the presence of water and ambient oxygen.

Compositions and Methods of Synthesis

CDMOF-2 can be prepared by reaction of γ-cyclodextrin [γ-CD] and rubidium hydroxide (RbOH) at room temperature in aqueous methanol (or ethanol). γ-CD is a cyclic oligosaccharide composed of eight D-glucopyranosyl residues linked 1,4 to each other. $Rb^+$ cations bind with γ-CD tori by coordinating to some of the ring oxygen atoms together with some of the secondary and primary hydroxyl groups at C-2, C-3 and C-6 on the glucopyranosyl rings. The coordination sphere round a particular $Rb^+$ cation is satisfied by eight oxygen atoms from four different γ-CD tori. This coordination geometry gives rise to a unit cell for CDMOF-2 (FIG. 1, panel (i)), comprised of six CD tori and 24 $Rb^+$ cations forming a cubic cage inside of which there exists a ~17 Å diameter void with two kinds of windows—a large circular one (windows) of diameter 7.8 Å and a smaller triangular-shaped one (windows) that is 4.2 Å from the apex to the opposite side of the triangle. Body centered cubic (bcc) close packing of the (γ-CD) unit cells produces a framework with the larger circular windows and the smaller triangular-shaped windows aligned, respectively, along the 100 and 111 axes in the crystal. $^{13}C$ NMR into the extended framework of CDMOF-2 results in covalent bonding of the $CO_2$ to the non-coordinated free primary hydroxyl groups, forming carbonic acid (CA) functions on the γ-CD tori to yield CA-CDMOF-2 (FIG. 1, (panel (ii)). For details of the synthesis and characterization of CDMOF-2, see U.S. Pat. No. 9,085,460 to Stoddart et al., entitled "NANOPOROUS CARBOHYDRATE FRAMEWORKS AND THE SEQUESTRATION AND DETECTION OF MOLECULES USING THE SAME", the contents of which is incorporated by reference in its entirety.

Methods of $CO_2$ Detection Using CDMOF-2

Figure 2A:
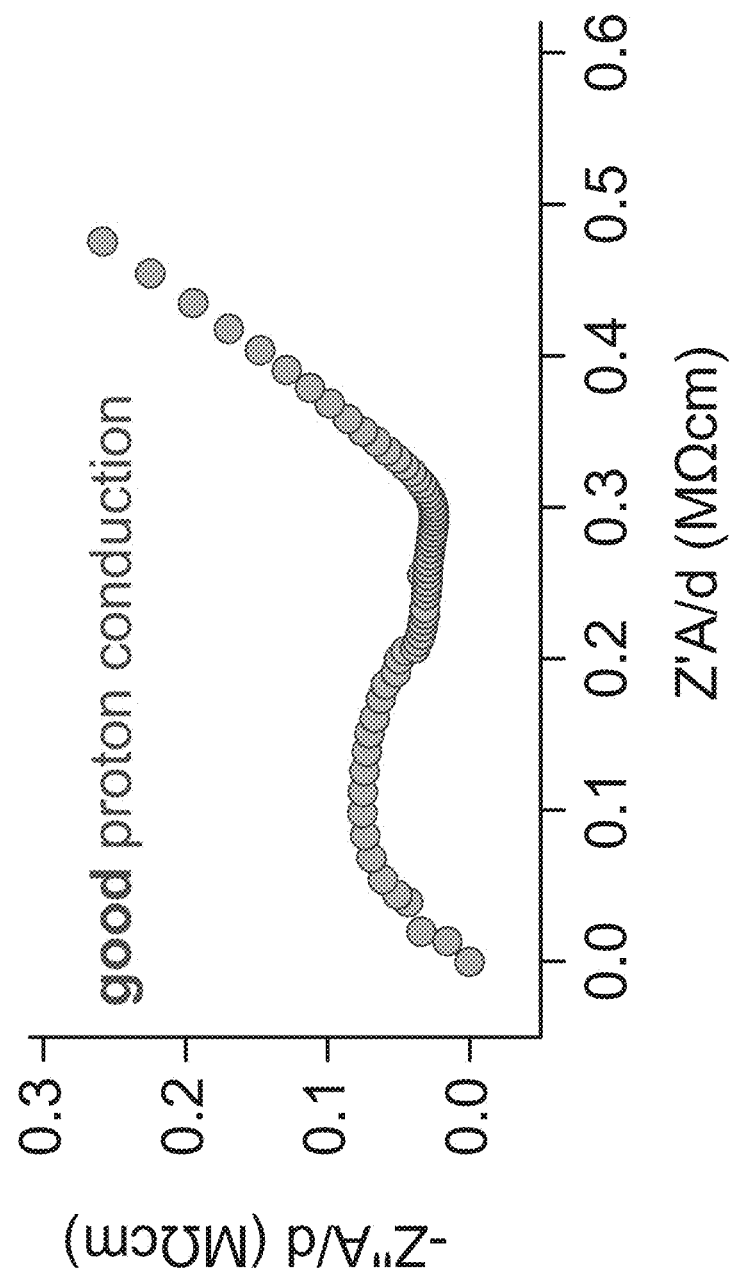
FIG. 2A depicts an exemplary impedance spectrum of a pristine CDMOF-2 sample following exposure to methanol vapor at room temperature.
Figure 2B:
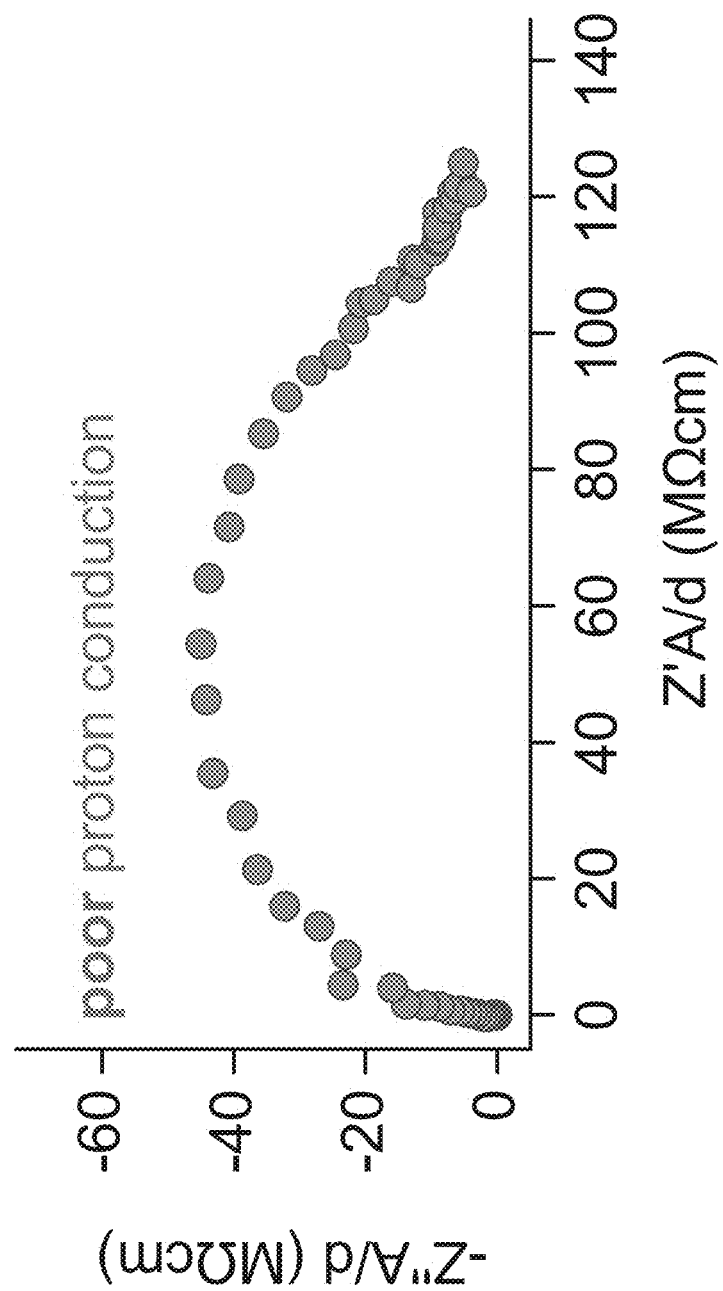
FIG. 2B depicts an exemplary impedance spectrum of a $CO_2$-infused CDMOF-2 sample following exposure to methanol vapor at room temperature.

Generally, MOFs containing hydroxyl functional group in their frameworks have been found to release protons into their nanopores or nanochannels with relatively low activation energies and thereby exhibit proton conduction. In a systematic investigation of the ionic conductivity of CDMOF-2, the 'as synthesized' version of CDMOF-2 and a $CO_2$ gas-infused species, CA-CDMOF-2, with methanol or n-hexane as a pore filling solvent was evaluated. Based on the greater acidity of carbonic acids relative to that of the primary alcohols, the $CO_2$-infused CA-CDMOF-2 was expected to show higher conductivity than pristine CDMOF-2. Surprisingly, CDMOF-2 exhibits a ~550-fold higher conductivity compared to that exhibited by CA-CDMOF-2 (see FIG. 2 and Table 1). The conductivity of pristine CDMOF-2 was measured to be ~4.8 $\mu Scm^{-1}$ while CA-CDMOF-2 is only 9 $nScm^{-1}$.

TABLE 1

Conductivities of CDMOF-2 samples before and after exposure to gas phase $CO_2$ for 5 min in various $CO_2$ concentrations.

| $CO_2$ conc. (%)[a] | $\sigma$ ($nScm^{-1}$) | | | | |
|---|---|---|---|---|---|
| | Sample 1 | Sample 2 | Sample 3 | Ave. | Ratio |
| 0 | 4740 | 4569 | 5095 | 4801 | 550 |
| 10 | 1069 | 1129 | 1248 | 1149 | 130 |
| 20 | 228 | 198 | 223 | 216 | 24 |
| 30 | 115 | 99 | 110 | 108 | 12 |
| 40 | 63 | 49 | 57 | 57 | 6.5 |
| 60 | 21 | 24 | 20 | 22 | 2.5 |
| 90 | 11 | 12 | 10 | 11 | 1.2 |
| 100 | 9 | 9 | 8 | 9 | 1.0 |

[a]The concentration of the $CO_2$ gas was controlled by mass flow controller, diluting with $N_2$ gas.

Without the claimed subject matter being bound or limited by any particular theory, this observation is tentatively attributed to the blockage of the hydrophilic, triangular-shaped windows with carbonates as the reaction proceeds. These windows are the sole location of all uncomplexed, primary alcohol functions and, consequently, the place where carboxylation occurs primarily.

Figure 3:
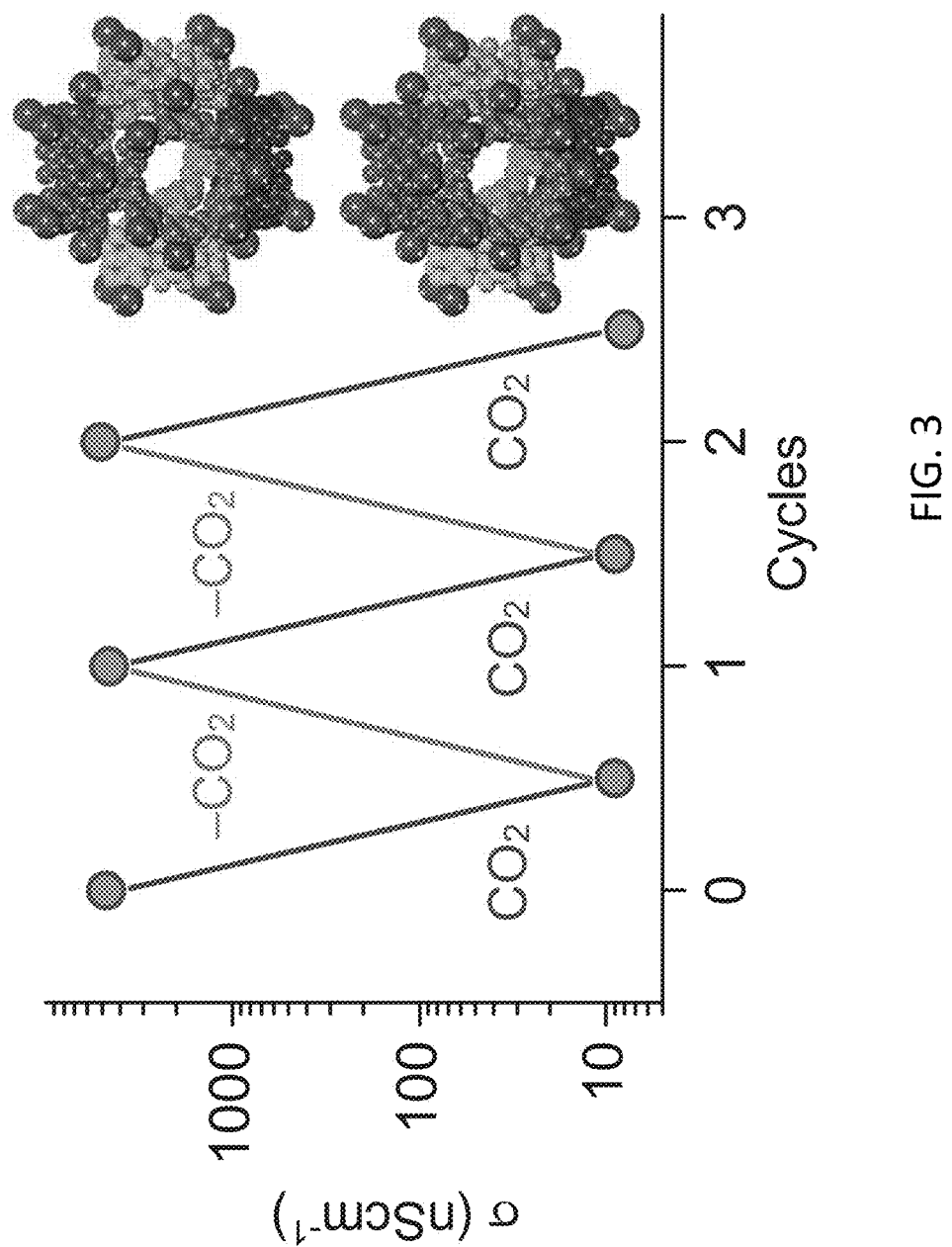
FIG. 3 depicts an exemplary plot showing the cyclic change of conductivity of a CDMOF-2 sample following sequential $CO_2$ sorption and desorption.

An attractive property of CDMOF-2 is the high degree of reversibility found in the chemisorption of $CO_2$. This reversibility, which occurs rapidly under very mild conditions, liberating the sequestered $CO_2$, is important in the continuous reusability of CDMOF-2. To this end, the cyclic changes in conductivity by a pellet of CDMOF-2 as a result of undergoing multiple chemisorption/desorption experiments of $CO_2$ were conducted. A pellet sample was prepared and the sample was exposed to $CO_2$ gas (99.8%, bone dry) for chemisorption, tested and then heated at ~80° C. for desorption and tested again. The conductivity of pristine CDMOF-2, which initially showed a high value, was decreased by a factor of ~550-fold after $CO_2$ sorption, but was once again reinstated after $CO_2$ desorption. This process is completely reversible (FIG. 3) over many iterations with no degradation in performance.

Figure 4:
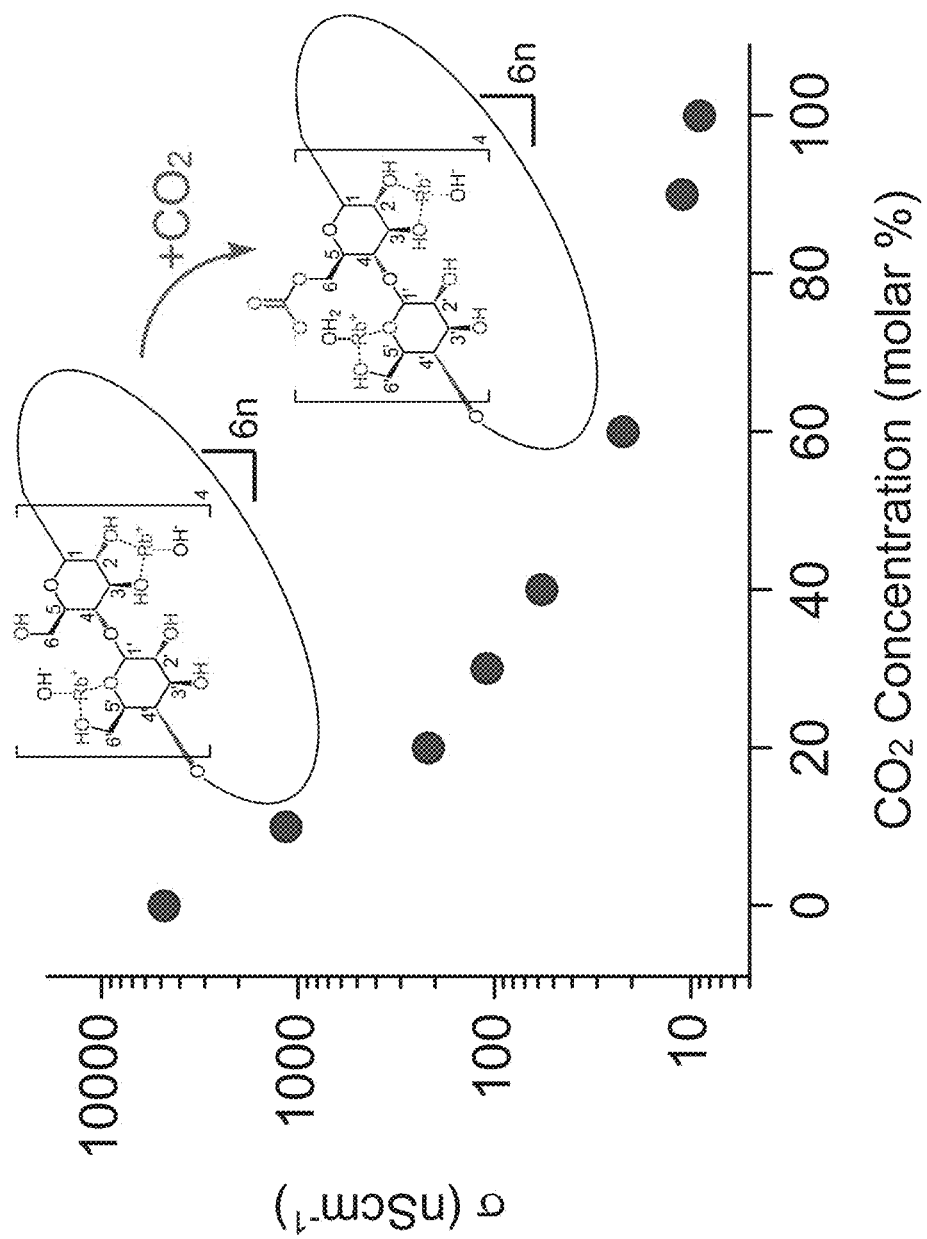
FIG. 4 depicts an exemplary exponential scale plot of average conductivity values in CDMOF-2 samples after their exposure for 5 min to $CO_2$ gas that was diluted with $N_2$ in various concentrations.
Figure 5:
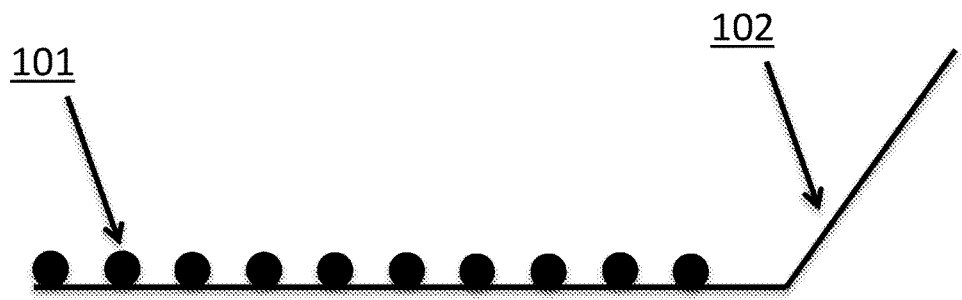
FIG. 5 depicts an exemplary embodiment of an electrochemical sensor composition (100) that includes a CDMOF-2 crystalline matrix in pellet form (depicted as black circles (101)) in electrical contact with indium-coated copper wire and conductive silver epoxy (102).

These experiments suggests that this MOF acts as a sensor for $CO_2$ in the presence of air, from which no effort was made to exclude extraneous water vapor or oxygen. With these results in hand, the device was tested to determine if it displays ratiometric responses to the amount of $CO_2$ present in a mixture of gases. Thus, the MOF was tested and the conduction responses at various $CO_2$ gas concentrations were recorded. The conductivity dropped down sharply (FIG. 4) as the $CO_2$ concentration was in creased. The slope shows a rough exponential decay as the concentration is decreased with better sensitivity in the low $CO_2$ concentration regime, compared with that at high concentrations. Based on this observation, the sensitivity of the MOF-sensor will be affected by several factors including: (i) the reactivity of carboxylation, (ii) the diffusion rate of $CO_2$ gas into pellets, (iii) the pellet thicknesses, and (iv) the exposure time of the sample to $CO_2$ gas. Based on the assumption that the reaction rate of carboxylation would be much faster than the $CO_2$ diffusion rate, the slope was used as a criterion of sensitivity in low $CO_2$ concentration region, which is expected to be steep when the pellet thickness is thinner and/or $CO_2$ exposure time is longer. Thin pellets or films will be more sensitive as a real time reporter. Accordingly, CDMOF-2 comprises a crystalline matrix preferably having a pellet or film form.

Applications

In a first aspect, an electrochemical sensor for an analyte is provided. The electrochemical sensor includes CDMOF-2. In a first respect, the analyte comprises $CO_2$. In a second respect, CDMOF-2 is prepared according to the process that includes two steps. The first step includes forming an aqueous mixture of γ-cyclodextrin and RbOH. The second step includes vapor-diffusing methanol into the aqueous mixture. In a further elaboration of the first aspect, the CDMOF-2 includes being electrically contacted with indium-coated copper wire and conductive silver epoxy. In a third respect of the first aspect, the $CO_2$ resides in a medium. In a further elaboration of the third respect of the first aspect, the medium includes a gas phase selected from air, air/$H_2O$ mixture, air/$O_2$ mixture and $CO_2$/$N_2$ mixture. In some respects, the medium includes a gas phase consisting of $CO_2$/$N_2$ mixture. In some respects, the sensor displays a ratiometric response to an amount of $CO_2$ present in the gas phase. In some respects, the amount of $CO_2$ present in the gas phase ranges from about 0% to about 100% $CO_2$. In some respects, the CDMOF-2 displays a conductivity decrease of ~550-fold after $CO_2$ sorption.

In a second aspect, a method of quantitatively detecting an analyte in a medium is provided. The method includes the step of contacting a CDMOF-2 with the medium. In some respects, the analyte includes $CO_2$. In some respects, the medium includes a gas phase selected from air, air/$H_2O$ mixture, air/$O_2$ mixture and $CO_2$/$N_2$ mixture. In some respects, the medium includes a gas phase consisting of $CO_2$/$N_2$ mixture. In some respects, the electrochemical sensor is made according to a process that includes several steps. The first step includes forming an aqueous mixture of γ-cyclodextrin and RbOH and vapor-diffusing methanol into the aqueous mixture, wherein the CDMOF-2 is formed. The second step includes electrically contacting the CDMOF-2 with indium-coated copper wire and conductive silver epoxy. In some respects, the sensor displays a ratiometric response to an amount of $CO_2$ present in the gas phase. In this respect, the amount of $CO_2$ present in the gas phase ranges from about 0% to about 100% $CO_2$. In this respect, the CDMOF-2 displays a conductivity decrease of ~550-fold after $CO_2$ sorption.

EXAMPLES

The invention will be more fully understood upon consideration of the following non-limiting examples, which are offered for purposes of illustration, not limitation.

Example 1. Materials and Methods

Materials.

All solvents and reagents were obtained from commercial sources (Sigma Aldrich, Wacker Chemical, Cambridge Isotopes, Airgas) and were used without further purification. Anhydrous MeOH (99.8%, Aldrich) was used after further drying with vigorously dehydrated zeolite 4A in moisture-free, argon-charged glove box. For the preparation of CDMOF-2, first, γ-cyclodextrin (1 mmol) and RbOH (8 mmol) were dissolved in deionized $H_2O$ (20 mL). After the solution had been filtered through a 13-mm syringe filter (0.45 m PTFE membrane) into pre-washed borosilicate culture tubes (16×150 mm), MeOH (ca. 50 mL) was allowed to vapor-diffuse into this gaseous solution over a period of two weeks. Eventually, colorless cubic single crystals were obtained and they were washed with MeOH twice prior to measuring the ionic conductivity. Pellets for conductivity measurements were electrically contacted using indium-coated copper wire (diameter=0.25 mm, Arcor) and conductive silver epoxy (type A and B, Chemtronix).

Instrumentation.

Dilution of $CO_2$ gas with $N_2$ was carried out using a mass flow controller (MKS instruments, M100B Mass-Flo® and Type 247 Power Supply/Readout for MKSMFC). Impedance spectra of the samples were recorded at ca. 50 mV in the frequency range of $0.1-2 \times 10^6$ by using a 1286 Electrochemical interface-equipped SI1260 Impedance/Gain Phase analyzer (Solartron Analytical). Measurements were performed at room temperature (ca. 296K).

REFERENCES

Gassensmith J J, Kim J Y, Holcroft J M, Farha O K, Stoddart J F, Hupp J T, Jeong N C. "A metal-organic framework-based material for electrochemical sensing of carbon dioxide," *J. Am. Chem. Soc.* 136:8277-82 (2014).

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. An electrochemical sensor composition for sensing an analyte, wherein the electrochemical sensor composition consists of CDMOF-2 being electrically contacted with indium-coated copper wire and conductive silver epoxy, wherein the CDMOF-2 has a crystalline matrix in a pellet form.

2. The electrochemical sensor composition of claim 1, wherein the analyte comprises $CO_2$.

3. The electrochemical sensor composition of claim 1, wherein CDMOF-2 is prepared according to the process comprising:
   forming an aqueous mixture of g-cyclodextrin and RbOH; and
   vapor-diffusing methanol into the aqueous mixture.

4. The electrochemical sensor composition of claim 2, wherein the $CO_2$ resides in a medium.

5. The electrochemical sensor composition of claim 4, wherein the medium comprises a gas phase selected from air, air/$H_2O$ mixture, air/$O_2$ mixture and $CO_2/N_2$ mixture.

6. The electrochemical sensor composition of claim 4, wherein the medium comprises a gas phase consisting of $CO_2/N_2$ mixture.

7. The electrochemical sensor composition of claim 6, wherein the sensor displays a ratiometric response to an amount of $CO_2$ present in the gas phase.

8. The electrochemical sensor composition of claim 7, wherein the amount of $CO_2$ present in the gas phase ranges from about 0% to about 100% $CO_2$.

9. The electrochemical sensor composition of claim 1, wherein the CDMOF-2 displays a conductivity decrease after $CO_2$ sorption.

* * * * *